(12) United States Patent
DeSilets et al.

(10) Patent No.: US 6,754,520 B2
(45) Date of Patent: Jun. 22, 2004

(54) MULTIMODALITY MEDICAL IMAGING SYSTEM AND METHOD WITH PATIENT HANDLING ASSEMBLY

(75) Inventors: Mark DeSilets, San Jose, CA (US); Timothy Buskard, Livermore, CA (US); Joseph Carter, Los Gatos, CA (US); Jacco Eerden, Eindoven (NL); Donald Wellnitz, Fitchburg, WI (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 317 days.

(21) Appl. No.: 10/039,796

(22) Filed: Oct. 19, 2001

(65) Prior Publication Data

US 2003/0078489 A1 Apr. 24, 2003

(51) Int. Cl.⁷ .................................................. A61B 5/05
(52) U.S. Cl. .................. 600/415; 600/407; 600/410; 600/425; 606/130; 382/131; 378/205; 256/363.04; 128/906
(58) Field of Search ................................. 600/407–436, 600/473–480; 382/131; 606/130; 250/363.04; 378/4, 21–27, 49, 87, 92, 205

(56) References Cited

U.S. PATENT DOCUMENTS

| | | | | |
|---|---|---|---|---|
| 5,178,146 A | * | 1/1993 | Giese | 600/411 |
| 5,349,956 A | * | 9/1994 | Bonutti | 600/425 |
| 5,525,905 A | * | 6/1996 | Mohapatra et al. | 324/318 |
| 5,562,094 A | * | 10/1996 | Bonutti | 600/415 |
| 5,851,182 A | * | 12/1998 | Sahadevan | 600/407 |
| 6,205,347 B1 | * | 3/2001 | Morgan et al. | 600/407 |
| 6,603,991 B1 | * | 8/2003 | Karmalawy et al. | 600/411 |

* cited by examiner

*Primary Examiner*—Brian L. Casler
*Assistant Examiner*—William C. Jung

(57) ABSTRACT

The invention comprises a system and method for handling a patient in a tomographic imaging system using a plurality of imaging devices. The imaging devices each have a bore through which a patient is translated during scanning. One or more patient support structures extend from the front of the tomographic imaging system, where the patient is initially placed, through the bores of the system. The patient is translated through the bores of the system and along the patient support structures by an actuator.

31 Claims, 6 Drawing Sheets

MULTIMODALITY MEDICAL IMAGING SYSTEM AND METHOD WITH PATIENT HANDLING ASSEMBLY

TECHNICAL FIELD

The invention relates to multimodality medical imaging systems for viewing anatomical structures and functions of a patient, such as combined x-ray Computed Tomography (CT) and Positron Emission Tomography (PET) scanners and, more particularly, to a patient handling assembly that reduces the overall length of the system.

BACKGROUND OF THE INVENTION

Tomographic imaging devices or cameras are frequently used to assist in the diagnosis and treatment of a variety of anatomical structures and physiologic functions within the body of a subject patient, while minimizing the need for invasive procedures. Such devices typically utilize scanners that obtain data or information about such structures and functions from the patient at specified, discrete locations along the length of a patient. Using this information, the camera produces a series of images, each depicting a cross-section of the body of the patient, in a plane generally perpendicular to the length of the patient, and at specified points along the length of the patient. Combined, successive images or a substantially continuous spiral image taken along the length of a patient can yield a relatively three-dimensional view of internal organs and tissues, or at least provide a cross-sectional view of bodily structures or functions at various places on the patient. Tomographic cameras are most frequently used to view and treat organs and other tissues within the head, torso and trunk of a patient and, in particular, diagnose and treat such ailments as heart disease, arteriosclerosis, cancer, and the like.

Tomographic imaging cameras are often identified by the "mode" or "modality" of radiation used by their scanners to obtain patient data. Well-known scanner modalities include the X-ray Computed Tomography (CT), Magnetic Resonance Imaging (MRI), Ultrasound (ULT), Single Photon Emission Computed Tomography (SPECT) and Positron Emission Tomography (PET) scanners. Camera systems which combine two or more different scanners to obtain a greater variety of imaging information from a patient are referred to as "multimodality imaging systems." Conversely, tomographic cameras utilizing the same mode to collect imaging information are referred to as having the same modality.

A tomographic camera utilizes a scanner having an array of radiation detectors forming a ring or bore that surrounds a patient. The scanner gathers information along a plane defined by the detector ring, which intersects the patient substantially perpendicularly to the length of the patient. Other processors and instruments coupled to the scanner form the tomographic image, based on information received from the scanner. To obtain information at successive points along the head, torso and trunk of a patient, the patient is supported horizontally on a patient table that translates or moves the patient horizontally through the bore of a tomographic camera.

It is often desirable to utilize two or more adjacent tomographic scanners of different modalities, in multimodality systems, to obtain a variety of imaging information from a single traverse of a patient through multiple scanner bores. This is highly desirable as a means of increasing efficiency (by completing two or more scans in one operation), increasing the accuracy of indexing, correlating or linking multimodality images to the same location along the length of the patient (by coordinating operation of the scanners to a single, controlled movement of the patient) and reducing the labor costs otherwise associated with separate, multimodality scanning operations.

In general, multimodality systems include a series of scanners, each having a different modality, supported by a single housing. Each scanner obtains different information about the patient, which, when registered in combination, provides a better understanding of the patient. More specifically, multimodality cameras typically include a scanner of anatomical structures of the patient (e.g., CT, MRI and Ultrasound cameras) and a scanner of physiologic functions of the patient (e.g., SPECT and PET cameras). The series of scanners forms a relatively long bore, typically longer than the combined head and torso of taller patients and spanning the entire length of shorter patients.

A patient table translates the patient through the scanners in a controlled manner, providing information to the system about the position of the patient. The position information it used to register the images formed from the scanner information to the same locations along the length of the patient. Unfortunately, conventional patient tables have a patient support surface that must be long enough to extend the patient from outside the first scanner bore, beyond the outlet of the final scanner bore. As a result, the patient support surface is typically longer than the entire length of the multimodality scanner assembly. Moreover, when the patient is positioned outside the scanner bores, at the front of the scanner assembly, the portion of the patient support surface extends forward from the assembly by a distance greater than the scanner assembly itself. This configuration is required particularly if the support surface is to be used to raise and lower the patient between the level of the scanner bores and the floor.

The combination of a lengthy multimodality scanner bore and longer patient support surface limit the facilities in which multimodality systems can be used, increase the cost of using and storing such systems and thus limit their availability. Accordingly, there is a need for a patient table for use in a multimodality tomographic imaging system that reduces the space required for use and associated costs.

SUMMARY OF THE INVENTION

The invention comprises a system and method for handling a patient in a tomographic imaging system using a plurality of imaging devices. The imaging devices each have a bore through which a patient is translated during scanning. One or more patient support structures extend from the front of the tomographic imaging system, where the patient is initially placed, through the bores of the system. The patient is translated through the bores of the system and along the patient support structures by an actuator.

In one aspect of the invention, a portion of the patient support structure extending from the front bore of the system is vertically adjustable, to position the patient in alignment with the scanner bores.

In another aspect of the invention, the patient is drawn through the scanner bores along the patient support structure by one or more belts.

In yet another aspect of the invention, the patient is supported on a pallet, which is drawn through the scanner.

In still another aspect of the invention, a portion of the patient support structure is positioned outside the bores at the front of the system, to vertically position the patient in alignment with the bores.

BRIEF DESCRIPTION OF THE DRAWINGS

For a more complete understanding of the present invention, and the advantages thereof, reference is now made to the following description taken in conjunction with the accompanying drawings, in which.

DETAILED DESCRIPTION

Figure 1:
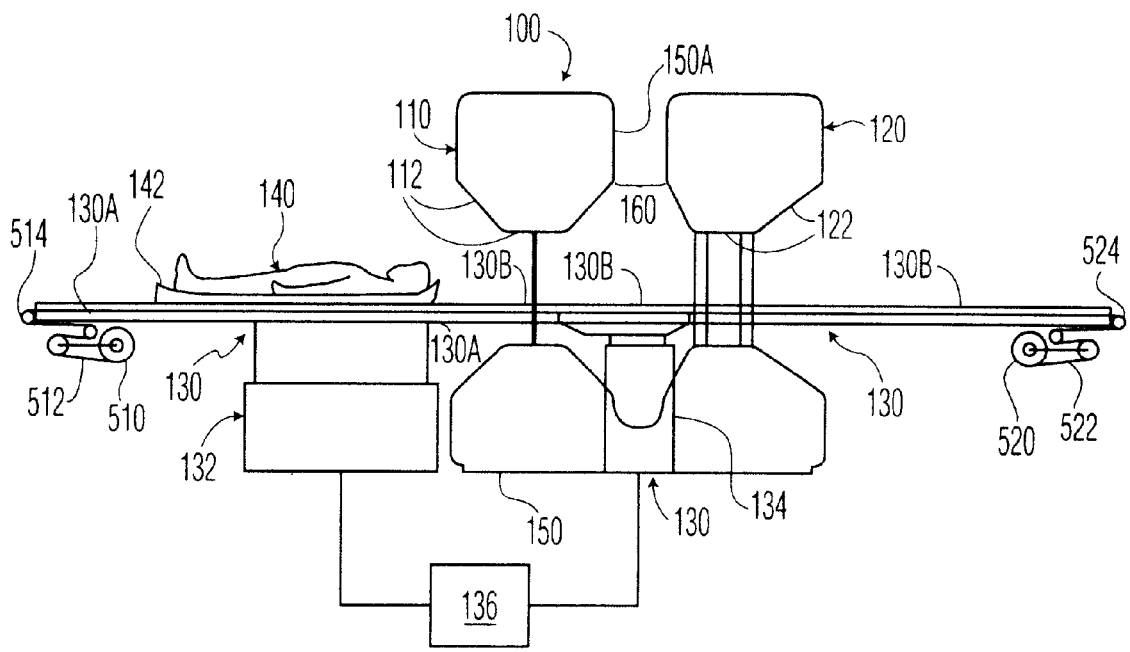
FIG. 1 is a schematic side view of a multimodality medical imaging system incorporating the present invention.
Figure 2:
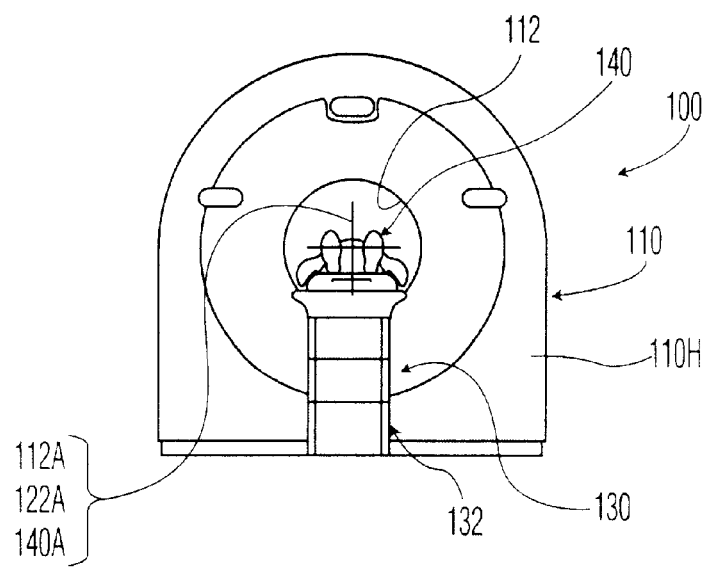
FIG. 2 is a front view of the multimodality medical imaging system of FIG. 1.

Shown in FIGS. 1 through 4 is a multimodality medical imaging system scanner assembly 100, having first and second imaging devices 110 and 120. In the embodiment shown, each of the imaging devices 110 and 120 comprise at least a scanner having a modality of operation, and may also include associated scanner support structure and associated electronics. Further, in the embodiment shown, each of the imaging devices 110 and 120 includes a scanner opening or bore 112 and 122, respectively, through which an inboard portion 130B of a patient table 130 extends and translates a subject patient 140 during a scanning operation. It will be apparent that imaging devices 110 and 120 may alternatively utilize scanners or detectors that obtain information about the patient 140 without being configured to form a bore, such as a partial closure, an arrangement of one or more planar detectors and other configurations capable of obtaining patient information. Moreover, it will be apparent that while scanner bores 112 and 122 are preferably circular, other configurations capable of obtaining imaging information may alternatively be utilized.

The patient table 130 serves as a patient handling assembly and support structure. The patient table 130 coordinates movement of the patient 140 with respect to operation of the scanners of the imaging devices 110 and 120, to obtain patient imaging information at one or more desired locations along the length of the patient 140. An outboard portion 130A of the patient table 130 includes a vertical actuator 132 for lifting and vertically aligning the longitudinal axis 140A of the patient 140 with the axes 112A and 122A of the bores 112 and 122. Inboard portion 130B of the patient table 130 also includes a vertical actuator 134 for aligning vertically with the outboard portion 130A of the table 130. In operation, the patient table 130 is capable of extending the patient 140 past the scanners of the imaging devices 110 and 120 in a variety of methods, such as at a continuous rate, at variable rates, in incremental displacements or a combination of such methods, as may be desired or suitable for the scanning operation to be conducted.

Figure 3:
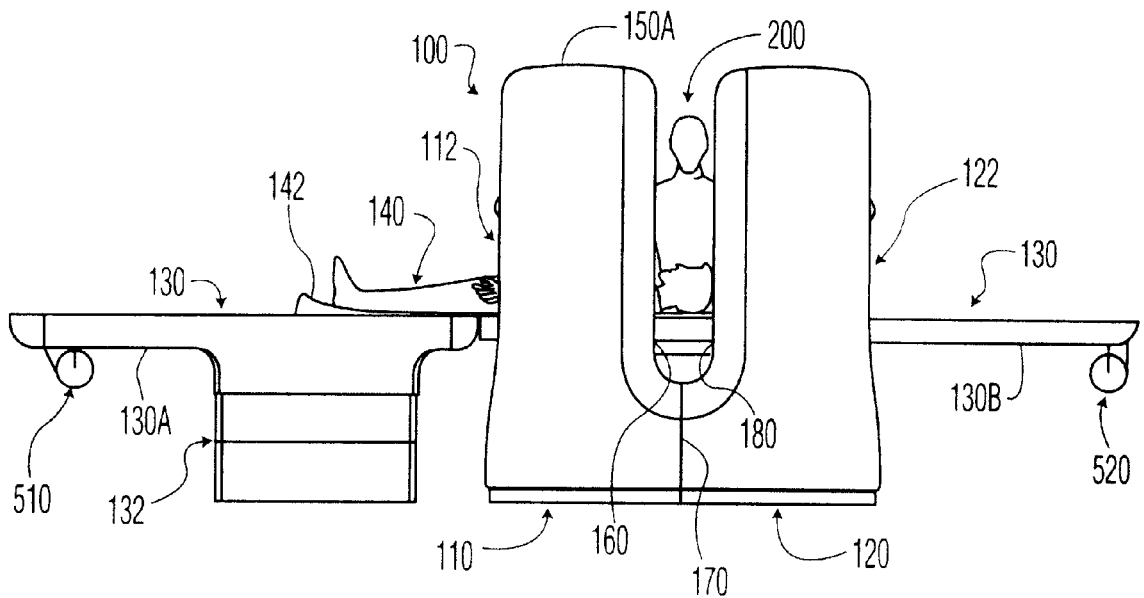
FIG. 3 is side view of the multimodality medical imaging system of FIG. 1, illustrating the imaging devices in a closed position.
Figure 4:
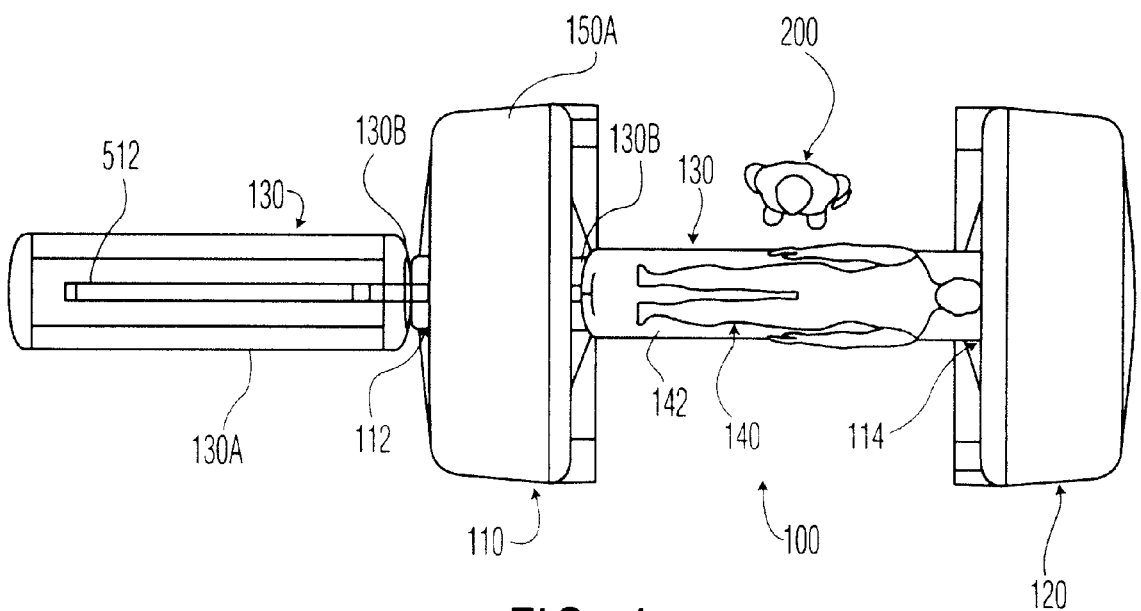
FIG. 4 is a top view of the multimodality medical imaging system of FIG. 1, illustrating the imaging devices in separate positions.

It will be apparent that the patient table 130 may be utilized in combination with the patient access area 160 and drainage surface 180, as shown in FIGS. 1 and 3, and with features allowing the separation of imaging devices 110 and 120 shown in FIG. 4. All such features are disclosed in co-pending U.S. application Ser. No. 10/027,843, entitled "Multimodality Medical Imaging System and Method With Intervening Patient Access Area" and naming as inventors Mark DeSilets, Jacco Eerden and Horace H. Hines and in co-pending U.S. application Ser. No. 10/051,490, entitled "Multimodality Medical Imaging System and Method With Separable Detector Devices" and naming as inventors Mark DeSilets, Horace H. Hines and Donald Wellnitz, both of which applications were filed on Oct. 19, 2001. The contents of both such applications are incorporated herein by reference for all purposes.

The imaging devices 110 and 120 acquire, through their scanners, information from the patient 140 sufficient to form tomographic images of the patient. Each of the imaging devices 110 and 120 is coupled to one or more conventional tomographic imaging processor(s), utilizing conventional imaging software to form images from information received from the imaging devices 110 and 120.

Preferably, the imaging devices 110 and 120 cooperate to obtain patient information through different modalities, to provide anatomical structure images and physiologic function images of the patient 140. More specifically, imaging device 110 is preferably a CT scanner that utilizes X-rays as the mode of obtaining data from which images depicting the internal structure of the patient 140 are formed. On the other hand, imaging device 120 is preferably a PET scanner that utilizes positron emissions originating from a radio-pharmaceutical introduced to the patient as the mode of acquiring data from which images depicting primarily metabolic physiological functions within the patient 140 are formed. During operation, the head and torso of the patient 140 are passed through the bores 112 and 122 of the respective imaging devices 110 and 120, and their respective scanners, so that a collection of one or more images are obtained from each scanner. When scanning is complete, the patient is retracted in the opposite horizontal direction by the patient table 130, typically at a faster rate than during the scanning operation, to withdraw the patient 140 from the scanner assembly 100, to the starting position at the beginning of the scanning procedure.

The scanner bores 112 and 122 of the imaging devices 110 and 120 are substantially circular, thus surrounding the patient during imaging scanning operations. The axes 112A and 122A of the respective circular openings of each of the bores 112 and 122 are aligned with each other and are preferably aligned with or at least substantially parallel to the path of travel of the patient 140 on the patient table 130. This allows the patient table 130 to translate the patient 140 through the imaging devices 110 and 120 in one substantially continuous pass. Preferably, the center line of the patient 140 is substantially aligned with or at least substantially parallel to the axes 112A and 122A of the detector bores 112 and 122 by adjusting the heights of the inboard and outboard patient table portions 130A and 130B adjusting vertical actuators 132 and 134, respectively.

Figure 5:
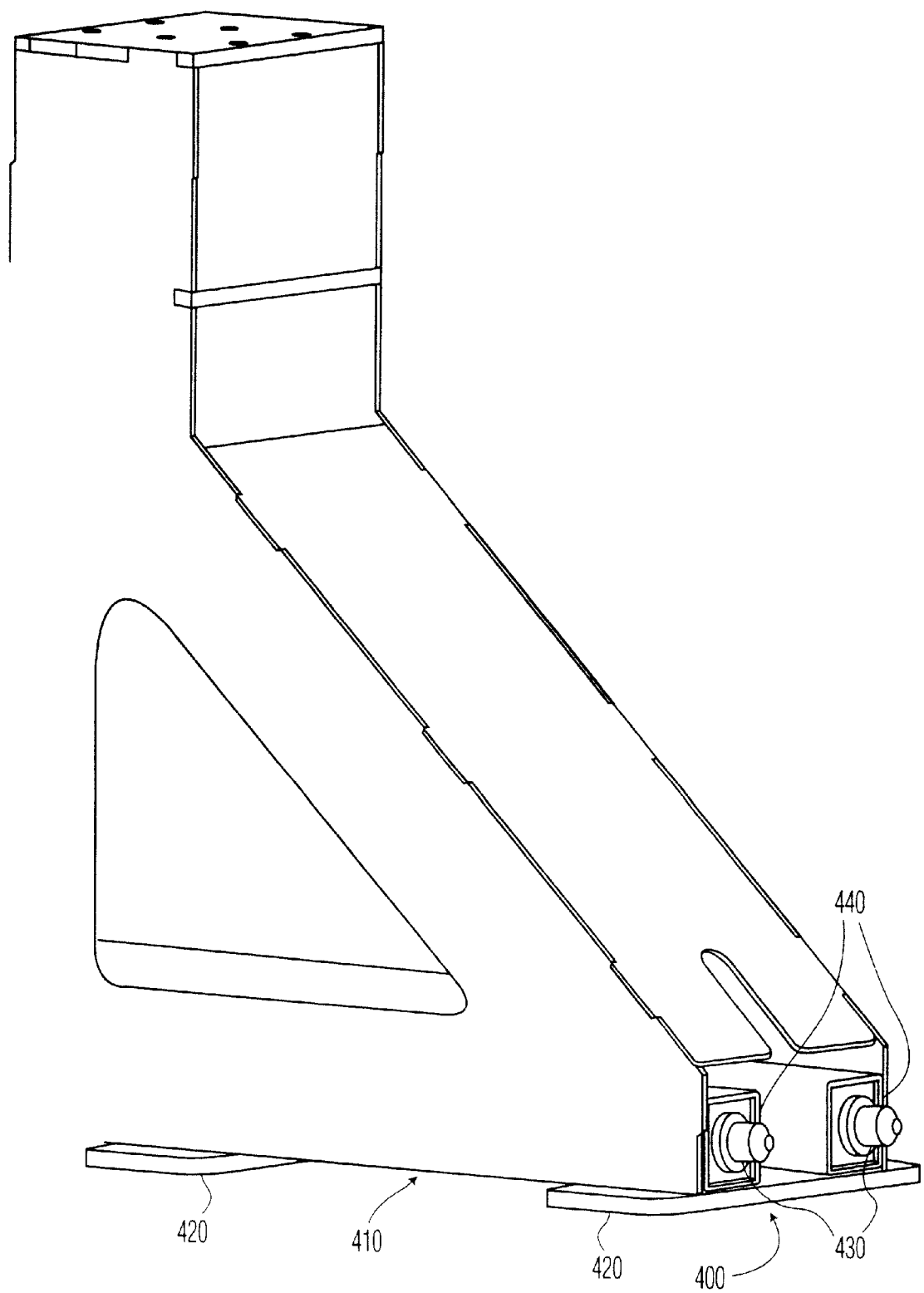
FIG. 5 illustrates a support frame for aligning the imaging devices in a closed position and for supporting a vertical actuator positioned between the imaging devices.

The outboard portion 130A of the patient table 130 includes a forward section cantilevered forward from the actuator 132. The table portion 130A terminates at the other end adjacent the inboard table portion 130B and adjacent the opening to bore 112 of the front imaging device 110. The inboard table portion 130B includes a section cantilevered forward into the scanning area of the front imaging device 110. A middle section of the table portion 130B extends between the imaging devices 110 and 120 and spans the patient access area 160. Extending rearwardly from the middle section is a rearward section of inboard table portion 130B, which extends through the bore 122 of the rear imaging device 120 and a distance beyond the bore 122 sufficient to allow scanning of the entire length of a patient. The vertical actuator 134 of the inboard table portion 130B is secured to the housing portion 150A of the front imaging device 110 and between the scanner bores 110 and 120. This is preferably accomplished by mounting the actuator 134 to the upper extension of a support frame 410, such as is shown in FIG. 5.

The position of the patient table outboard and inboard portions 130A and 130B are coordinated by a controller 136. The controller 136 obtains feedback signals from the vertical actuators 132 and 134 identifying the vertical positions of the table portions 130A and 130B. As outboard table portion 130A is raised to a vertical position substantially level with the neck of the bore 112, the controller 136 adjusts the actuator 134 to maintain vertical alignment between the inboard and outboard table portions 130A and 130B. The controller 136 preferably utilizes one or more conventional digital processors and associated memory to implement available software to coordinate and control the height of the table portions 130A and 130B. This coordination provides a substantially continuous support surface for the translation of the patient 140 from the outboard table portion 130A to the inboard table portion 130B.

The vertical actuators 132 and 134 are vertically extended by a variety of mechanisms, such as a scissor actuator, stacked lead screw, four bar linkage lifting mechanism, and the like.

The forward and rearward sections of the inboard table portion 130B are formed from a material that is translucent to radiation or other medium used by the imaging devices 110 and 120. This allows the forward and rearward sections of the table portion 130B to extend within the scanner bores 112 and 122 to support the patient 140 during translation, without blocking the imaging process. The construction of forward and rearward sections of the inboard table portion 130B is preferably a foam core, tightly wrapped by carbon fiber for additional strength and durability. It will be apparent that other materials could be used to wrap and strengthen the foam core of the forward and rearward sections of the table portion 130B. The middle section of the table portion 130B is constructed of any durable material and need not be translucent to scanner radiation.

The patient 140 is supported on the table 130 by a patient pallet 142. Because the weight of the patient 140 is supported by the substantially continuous surface of the patient table 130, the patient pallet 142 is constructed of very thin material, offering little attenuation to the radiation or other medium used by the imaging devices 110 and 120. Such materials are preferably similar to those available for use as a cover for the inboard table portion 130B. The pallet 142 is driven between the ends of the patient table 130 to translate the patient 140 as desired. The table 130 includes a drive assembly for driving the patient pallet 142 and the patient 140 between the ends of the patient table 130 during scanning operations.

The drive assembly comprises a pair of drive mechanisms 510 and 520, mounted at the forward and rearward ends, respectively, of the patient table 130. In addition, the drive assembly includes a forward drive belt 512 and a rearward drive belt 522, extending from the drive mechanisms 510 and 520, respectively. Each drive mechanism 510 and 520 comprises a servomotor and belt take-up reel mechanically coupled to an associated drive mechanism. A conventional controller (not shown) actuates the drive mechanisms 510 and 520 to apply substantially continuous tension to the drive belts 512 and 522. This allows more precise control of the position of the patient pallet 142 and avoids jerking the pallet 142 in the direction of actuation a distance greater than desired when moving the pallet 142 in incremental distances along the table 130. Tension in the drive belts 512 and 522 is maintained by actuating the servomotor drive mechanisms 510 and 520 in opposite directions, while applying greater tension in the direction movement is desired.

Figure 6:
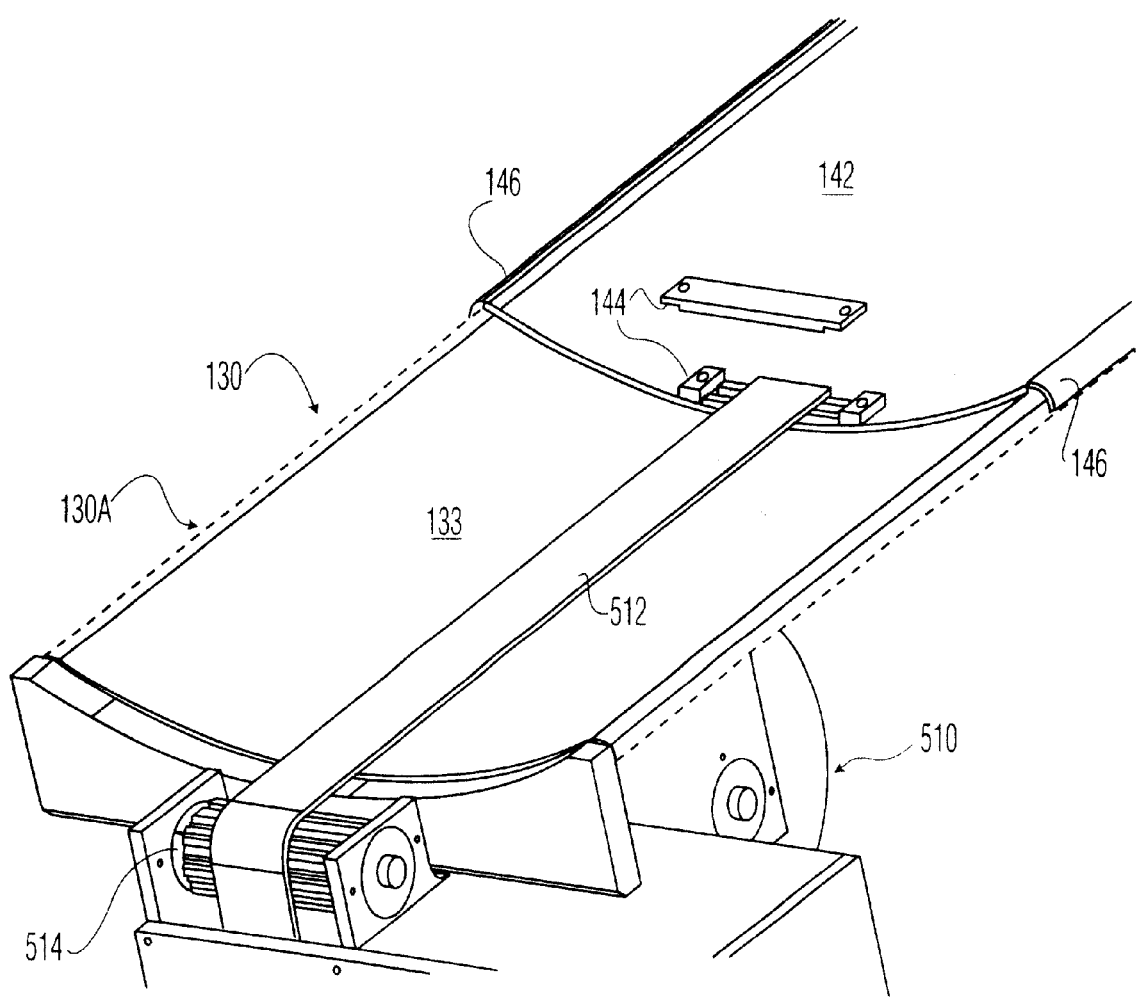
FIG. 6 is a perspective view of a front portion of a patient table and drive assembly of the patient handling assembly of the invention.
Figure 7:
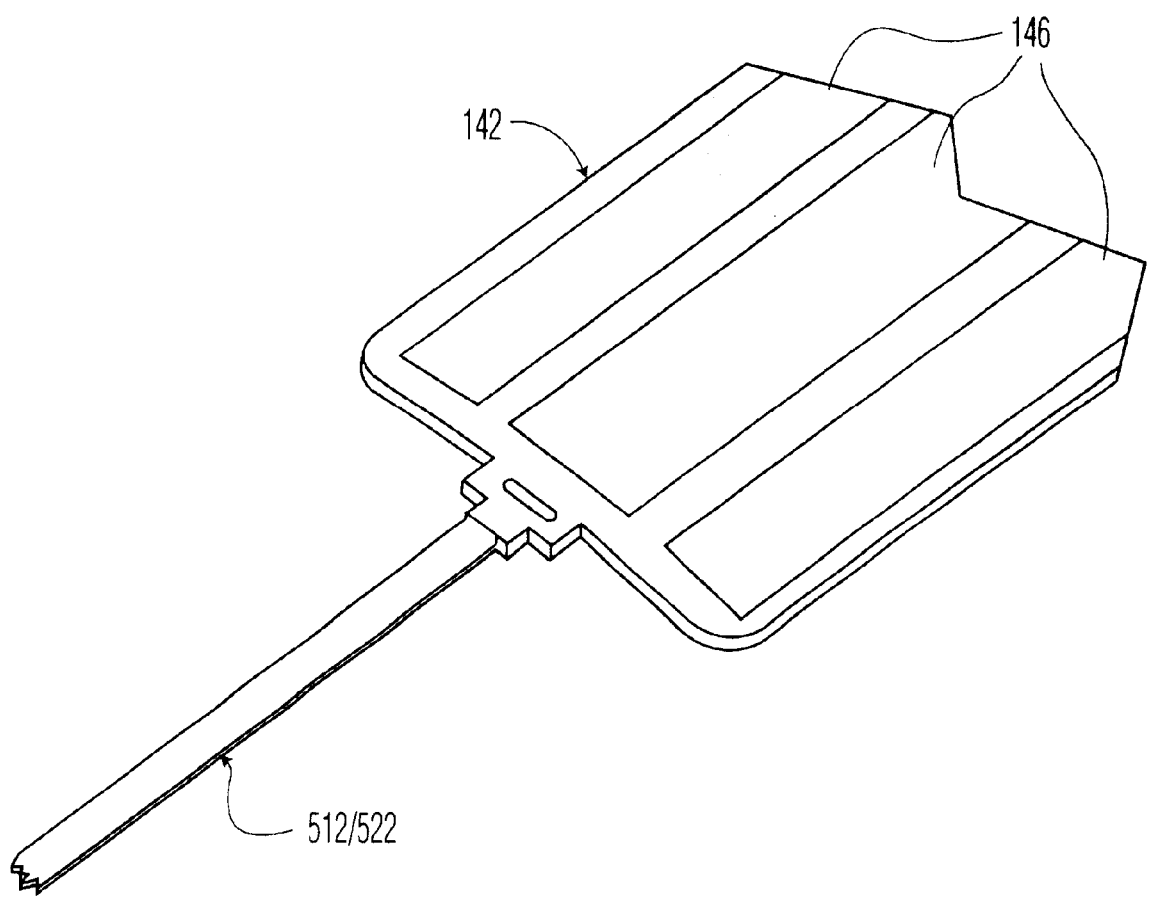
FIG. 7 is a perspective view of the underside of a patient pallet of the patient handling assembly.
Figure 8:
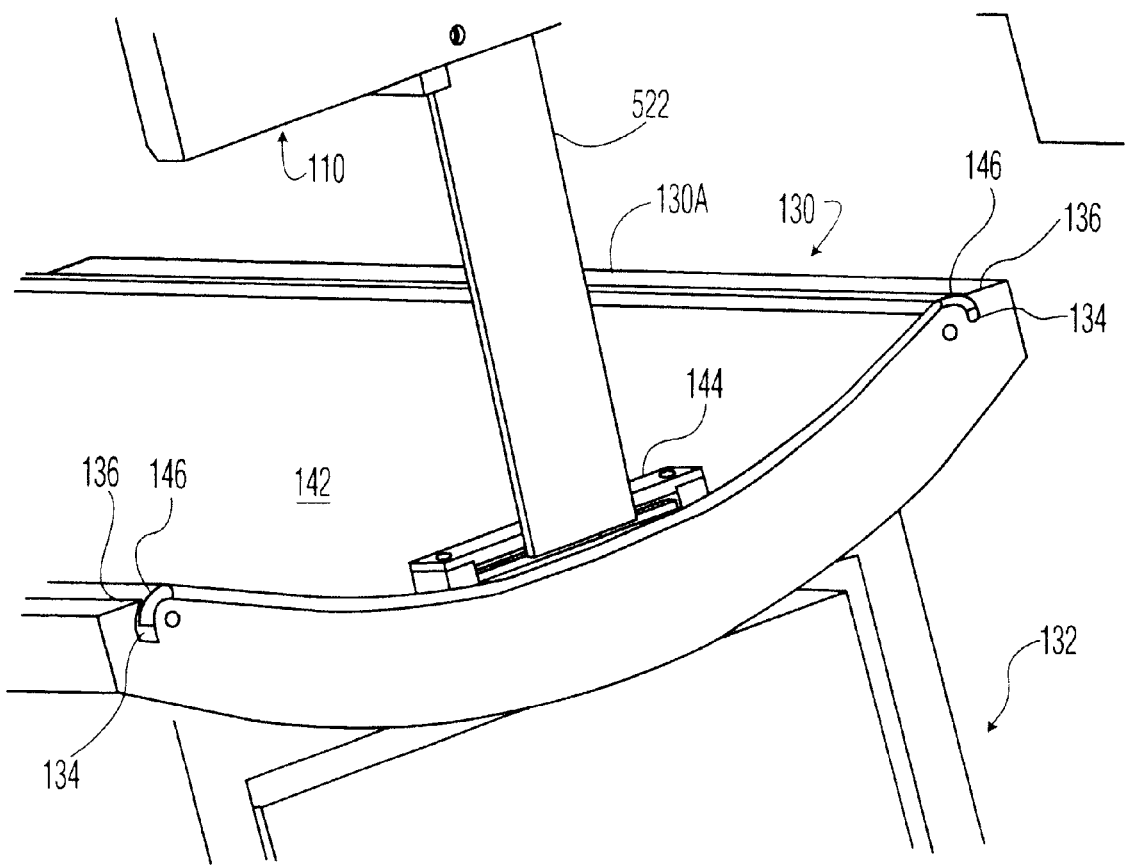
FIG. 8 is a perspective view of the front portion of the patient table of the patient handling assembly, looking forward from a position below the scanner of the front imaging device.

Referring now to FIGS. 6, 7 and 8, the construction and operation of the drive assembly, and various components of the patient table 130, are illustrated in more detail. The patient pallet 142 and the underlying support surface 133 of the patient table 130 are concave with respect to their longitudinal axes. This configuration cradles the patient 140 against rolling off the sides of the table 130. The drive belts 512 and 522 are preferably timing belts, which engage teeth in idler rollers 514 and 524, mounted at the forward and rearward ends, respectively, of the patient table 130. The drive belts 512 and 522 are secured to the respective front and rear ends of the patient pallet 142 by a clamp 144 that engages one or more of the teeth of the associated drive belts 512 or 522. To reduce friction between the patient pallet 142 and the underlying support surface 133 of the patient table 130, Teflon® strips 146 are bonded along the length of the underside of the patient pallet 142. The support surface 133 is preferably also covered with Teflon® material.

Utilizing a drive mechanism that does not require lateral movement of the sections of the inboard table portion 130B through the scanner bores 112 and 122 enhances the quality of the images obtained by the imaging devices 110 and 120. Because these sections remain still during scanning, the likelihood of new artifacts being introduced to an image or any the artifacts within the table 130 moving during scanning is avoided. Any artifacts within such sections of the table portion 130B that are within scanning areas may thus be identified and the image adjusted or interpreted accordingly.

Referring now in particular to FIGS. 6 and 8, there is shown a configuration of the patient pallet 142 and the outboard portion 130A of the patient table 130 forming a trapping mechanism that secures the pallet 142 against vertical movement in response to tension from the rearward drive belt 522. As is best shown in FIG. 8, the outboard actuator 132 is capable of lowering the outboard portion 130A of the patient table 130 to a height of approximately 19 to 20 inches above the floor, which is approximately the same height as a standard wheelchair. This facilitates transferring a patient 140 from a wheelchair to the patient table 130. In this position, the drive belt 522 extending from the rearward end of the patient table 130 extends downwardly from the forward section of the inboard section 130B of the patient table 130. This vertical separation of the forward and rearward table portions 130A and 130B is necessitated by the bore 112 of the imaging device 110, which blocks further downward movement of the inboard portion 130B of the patient table 130. Once the outboard portion 130A of the patient table 130 is raised upwardly into vertical alignment with the inboard section 130B, tension from the drive belt 522 becomes horizontal.

The pallet 142 includes downwardly curved trap segments 146 formed along the longitudinal edges. The trap segments 146 extend into curved trap slots 134 formed along the lateral edges of the outboard portion 130A of the patient table 130. The trap slots 134 curve upwardly over portions of the trap segments 146 of the pallet 142, forming trap shoulders 136. When a vertical force is applied to the pallet 142, the upper surfaces of the trap segments 146 of the pallet 142 abut the trap shoulders 136 of the table portion 130A to secure the pallet 142 against upward movement. Moreover, the upward force exerted against the middle section of the patient pallet 142 tends to laterally extend the trap segments 146 into the trap slots 134 as the concave pallet 142 tends to flatten. This response further secures the pallet 142 against vertical movement. Once the upward table portion 130A is vertically aligned with the inboard portion 130B, horizontal tension on the pallet 142 by the rearward drive belt 522 slides the pallet 142 horizontally towards the rearward end of the patient table 130. As the pallet 142 slides rearwardly, the trap segments 146 slide longitudinally out of engagement with the trap slots 134 and trap shoulders 136 of the outboard table portion 130A.

During operation, a patient 140 is placed on the patient pallet 142, with the outboard table portion 130A in a lowered position. The actuator 132 then lifts the support surface 133, pallet 142 and the patient 140 vertically into alignment with the inboard table portion 130B. Inboard table portion 130B tracks any further upward movement of the outboard table portion 130A in response to commands received from the actuator controller 136. Both the outboard table portion 130A and the inboard table portion 130B are vertically adjusted to align the longitudinal patient axis 140A with the aligned scanner bore axes 112A and 122A. Tension is increased in the rear drive belt 522 to pull the patient pallet 142 and the patient 140 at a desired rate through either or both of the imaging devices 112 and 122. Each of the drive mechanisms 110 and 520 include encoders that provide information concerning the position of the patient pallet 142 to an imaging processor (not shown), which registers the images formed from one or both of the imaging devices 110 and 120 to specific locations along the length of the patient 140.

It will be appreciated that use of the patient handling assembly disclosed avoids the need to translate the outboard and inboard portions 130A and 130B axially relative to the imaging devices 110 and 120. Instead, the table portions 130A and 130B are adjusted in a vertical direction. This reduces the amount of space required for the imaging system and its associated costs while also providing a front loading table portion 130A which is capable of independently lifting a patient 140 from the height of a wheelchair.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

What is claimed is:

1. A medical imaging apparatus comprising:
    a first imaging device for obtaining one or more tomographic images of a subject patient, at least a portion of the first imaging device having a first bore through which a patient pallet axially translates during formation of one or more images by the device;
    a first patient support structure for supporting the patient pallet in substantial alignment with the first bore of the first imaging device, the first patient support structure adapted to lift the patient pallet from a loading position below the first bore to a scanning position in substantial alignment with the first bore;
    a second patient support structure for supporting the patient pallet in substantial alignment with the first bore, which second structure extends into the first bore for receiving the patient pallet from the first patient support structure; and
    a patient positioning device for translating the patient pallet from the first patient support structure into the first bore and onto the second patient support structure without substantial movement of the first patient support structure towards the first bore, which positioning device includes:
        belt drive mechanisms which are disposed on opposite ends of the first and second support structures and pull the patient pallet across the first and second support structures in forward and reverse directions.

2. The imaging apparatus of claim 1,
    wherein the patient positioning device translates a patient from the first support structure onto the second support structure without substantial movement of the second patient support structure toward or away from the first bore.

3. The imaging apparatus according to claim 2, further including one or more actuators for vertically aligning the first and second patient support surfaces prior to translation of the patient by the patient positioning device from the first support structure onto the second patient support structure.

4. The medical imaging apparatus of claim 1, wherein the first medical imaging device is a multimodality tomographic imaging device.

5. A patient table for imaging a patient in a first modality which defines a first bore in which a patient is imaged and a second modality which defines a second bore in which the patient is imaged, the table including:
    a first patient support structure which terminates adjacent the first bore of the first modality;
    a second patient support structure adjacent to the first support structure which extends longitudinally through at least first and second bores of associated first and second modalities;
    a first vertical actuator, on which the first support structure is disposed to be moved vertically up and down with respect to the second support structure;
    a second vertical actuator, on which the second support structure is disposed and which second actuator aligns the second support structure with the first support structure;
    a patient pallet for supporting the patient on the first and second patient support structures; and
    a tether secured to opposing ends of the patient pallet and to a drive mechanism, which tether pulls the patient pallet across the first and second support structures into the first and second bores and extends downwardly from the opening of the first bore onto the first support structure when the first support structure is lowered with respect to the second support structure.

6. The patient table for imaging of claim 5, wherein the second patient support structure extends from the first bore in a direction away from the first patient support structure and for a distance outside the first bore at least as great as the length of the patient and wherein the patient is translated across substantially the entire length of the second patient support surface.

7. The medical table of claim 5, wherein the drive mechanism is secured on opposing ends of the first and second support structures and the patient pallet slides along the first and second support structures as the tether is retracted by the drive mechanism.

8. A medical imaging apparatus comprising:
a first tomographic medical imaging device having a first opening for receipt of a subject patient;
a second tomographic medical imaging device having a second opening for receipt of the subject patient;
a patient support structure extending through the openings of the first and second imaging devices;
a pallet for supporting a patient on the patient support structure for translation through the first and second openings of the first and second tomographic imaging devices to position the patient for formation of one or more images by at least one of the imaging devices;
the patient support structure having a cantilevered portion which is at least as long as the pallet extending through the opening of the second imaging device; and
a drive mechanism for sliding the pallet along the patient support structure and through the first and second openings of the first and second imaging devices.

9. The medical imaging apparatus comprising:
a first tomographic medical imaging device housed in a first housing defining a first closed bore for receipt of a subject patient;
a second tomographic medical imaging device housed in a second housing defining a second closed bore for receipt of the subject patient, the first and second bores being axially aligned and spaced by a the distance less than a length of the pallet and sufficiently large to allow direct tactile contact between a caregiver and the subject patient, when the first and second housing are positioned abutting each other;
a patient support structure extending through the bores of the first and second imaging devices;
a pallet for supporting a patient on the patient support structure for translation through the first and second axially aligned bores; and
a drive mechanism for moving the pallet along the patient support structure and through the first and second bores to position the subject patient for formation of one or more images by at least one of the imaging devices.

10. The medical imaging apparatus of claim 8, wherein the distance between the first and second openings allows a caregiver to perform one or more interventional applications on the subject patient between the first and second imaging devices.

11. The medical imaging apparatus of claim 10, wherein the distance between the first and second openings allows a caregiver to perform at least a portion of a biopsy procedure on the subject patient.

12. The medical imaging apparatus of claim 8, wherein the first imaging device comprises one of a group consisting of CT, MRI, X-Ray, and Ultrasound devices.

13. The medical imaging apparatus of claim 8 or 12, wherein the second imaging device comprises one of a group consisting of SPECT and PET devices.

14. The medical imaging apparatus of claim 8, wherein the axes of the first and second openings of the first and second imaging devices are substantially aligned.

15. The apparatus of claim 8, wherein the patient support structure includes a first section and a stationery second section which extends through the first opening and is cantilevered in a direction of the second imaging device and further including:
a drive mechanism for moving the second imaging device axially relative to the cantilevered second section between a position adjacent the first imaging device and a separated position to increase an access area between the first and second imaging devices.

16. A medical imaging apparatus, comprising:
a first shaped housing supporting a first tomographic scanner having a first bore for obtaining tomographic imaging information from at least a portion of a patient;
a second shaped housing supporting a second tomographic scanner having a second bore for obtaining tomographic imaging information from at least a portion of the patient, the first and second bores being axially aligned;
a guide rail substantially aligned with the axes of the first and second bores; and
a drive assembly which moves at least one of the first and second housings relative to the other housing in a direction substantially aligned with the guide rail to position the first and second housings between an abutting, joined position, with the axes of the first and second scanner bores substantially aligned, and a separated position.

17. The medical imaging apparatus of claim 16, wherein the first and second housings are shaped to define a patient access area between the first and second scanner bores when placed in the adjoining position, the access area allowing direct access by a caregiver to a patient extending through the first scanner bore and at least partially positioned between the first and second scanners.

18. The medical imaging apparatus of claim 16, wherein the first and second scanners are adapted to operate in different modalities with respect to each other.

19. The medical imaging apparatus of claim 18, wherein one of the first and second scanners is adapted to obtain imaging information representing anatomical structures of the patient.

20. The medical imaging apparatus of claim 18 or 19, wherein one of the first and second scanners is adapted to obtain imaging information representing physiologic functions of the patient.

21. A medical imaging method, comprising:
providing a first housing supporting a first tomographic scanner having a first bore for obtaining tomographic imaging information from at least a portion of a patient;
providing a second housing supporting a second tomographic scanner having a second bore for obtaining tomographic imaging information from at least a portion of the patient;
connecting the first and second housings by an actuator; and
actuating the actuator to position each of the first and second housings between an adjoined connected position, with the axes of the first and second scanner bores substantially aligned, and a separated position, with the scanner bores spaced from each other by the linear actuator.

22. The medical imaging method of claim 21, further comprising operating the first and second scanners in different modalities with respect to each other when the first and second scanners are in the adjoining position to obtain imaging information from the patient.

23. The medical imaging method of claim 22, further comprising operating one of the first and second scanners in a modality obtaining imaging information representing anatomical structures of the patient when the first and second scanners are in the separated position.

24. The medical imaging method of claim 22, further comprising operating one of the first and second scanners in a modality obtaining imaging information representing physiologic functions of the patient.

25. The medical imaging method of claim 21, further comprising forming a patient access area between the first and second scanners bores when the first and second housings are placed in the adjoining position, the access area allowing direct access by a caregiver to a patient extending through the first scanner bore and at least partially positioned between the first and second scanners.

26. A pallet supported by at least one support member for supporting a patient for translation through a medical imaging device, which pallet is driven by a pair of belts, the pallet comprising:

a support member formed of a material translucent to radiation and having an upwardly facing concave surface for supporting a patient;

the support member having a plurality of side edges substantially aligned with the trough of the concave curvature of the support member;

the side edges each having at least one segment for securing the support member against upward movement away from an underlying patient support table; and the securing segments allow the patient support member to be translated continuously across at least a portion of an underlying support table.

27. The pallet of claim 26, further comprising:

low friction material forming at least a portion of the downwardly facing surface of the support member for abutting the surface of an underlying support table.

28. The pallet of claim 26, wherein the securing segments comprise extensions for insertion in one or more slots of an underlying support table.

29. The pallet of claim 28, wherein exertion of an upward force against the support member when the securing segments are held against upward movement tends to laterally extend the segments into slots of an underlying support table.

30. The pallet of claim 28, further comprising one or more fasteners positioned at one end of the support member for attachment to a drive mechanism for translating the support member along an underlying support table.

31. The pallet of claim 28, wherein the support member comprises a foam core surrounded by carbon fiber.

* * * * *